US006342080B1

(12) United States Patent
Konaka

(10) Patent No.: US 6,342,080 B1
(45) Date of Patent: Jan. 29, 2002

(54) CANDLE

(75) Inventor: Masayoshi Konaka, Tokyo (JP)

(73) Assignee: Nippon Kodo Co. Ltd., Tokyo (JP)

( * ) Notice: Subject to any disclaimer, the term of this patent is extended or adjusted under 35 U.S.C. 154(b) by 0 days.

(21) Appl. No.: 09/678,332

(22) Filed: Oct. 3, 2000

(30) Foreign Application Priority Data

Oct. 4, 1999 (JP) .......................................... 11-282995

(51) Int. Cl.[7] ............................ C11C 5/00; A61L 9/02
(52) U.S. Cl. ............................ 44/275; 431/4; 431/288
(58) Field of Search ............................ 44/275; 431/4, 431/288

(56) References Cited

U.S. PATENT DOCUMENTS 3,582,251 A * 6/1971 Concannon et al. ........... 431/4
3,630,697 A * 12/1971 Duling ........................ 44/275
4,118,203 A * 10/1978 Beardmore .................. 44/275
4,449,987 A * 5/1984 Lindauer ..................... 44/275
5,891,400 A * 4/1999 Ansari et al. ............... 422/125
6,150,538 A * 11/2000 Delphis ...................... 542/266

FOREIGN PATENT DOCUMENTS

EP 1090976 A1 * 4/2001
WO WO00/26285 * 5/2000

* cited by examiner

*Primary Examiner*—Margaret Medley
(74) *Attorney, Agent, or Firm*—Zito & Grandinetti; Joseph J. Zito; Kendal M. Sheets

(57) ABSTRACT

A candle is disclosed, containing a candle-forming component including a paraffin wax and stearic acid, added and mixed with Tetrahydro methylabietate and dihydro Methylabietate, Isopropyl Myristate, α-Amylcinnamic Alcohol, Iso Bornyl Cyclohexanol, and Tri Ethyl Citrate. The candle has an effect for suppressing the exhalation of a nasty odor (an odor at extinguishing) generated when a flame has been extinguished, as well as an effect that, when the odor at extinguishing is vaporized by heat and diffused into air, molecules of various odors hanging in the air are trapped, whereby the air in the whole of a room is made refreshed.

1 Claim, 2 Drawing Sheets

CANDLE

BACKGROUND OF THE INVENTION

1. Field of the Invention

The present invention relates to a candle, and more specifically, to a candle that is made possible to suppress the exhalation of a nasty odor (an odor at extinguishing) generated when a flame has been extinguished.

2. Description of the Conventional Art

Regarding a candle, when a flame has been extinguished, a smoke in the white mist-like state as well as a characteristic nasty odor is exhaled. In this regard, it is considered that when a paraffin wax is melted due to the flame and its vaporized amount is in excess, this odor is generated. And, since this odor is offensive to the nose and gives an unpleasant feeling, improvements were being demanded.

SUMMARY OF THE INVENTION

Under such a background, the present inventor made extensive and intensive investigations on various substances. As a result, it has been found that the desired object can be attained by adding and mixing tetrahydro methylabietate and dihydro methylabietate, isopropyl myristate, α-amylcinnamic alcohol, iso bornyl cyclohexanol, and tri ethyl citrate, leading to the accomplishment of the invention.

Specifically, the gist of the invention is to provide a candle comprising a candle-forming component including a paraffin wax and stearic acid, added and mixed with tetrahydro methylabietate and dihydro methylabietate, isopropyl myristate, α-amylcinnamic alcohol, iso bornyl cyclohexanol, and tri ethyl citrate.

DESCRIPTION OF THE PREFERRED EMBODIMENT

An embodiment of the invention will be described below.

A candle according to the invention comprises a candle-forming component including a paraffin wax and stearic acid, added and mixed with Tetrahydro Methylabietate and dihydro methylabietate, isopropyl myristate, α-amylcinnamic alcohol, iso bornyl cyclohexanol, and tri ethyl citrate. Incidentally, since a process for the production of the candle of the invention is the same as in the conventional art, its explanation is omitted.

Further, the action and function of suppressing the exhalation of a nasty odor (odor at extinguishing) generated when a flame has been extinguished, by adding and mixing the above-described additives, are not always clear. But, it may be considered that since these additives are of a high boiling point and control the components to be not boiled, a vaporization pressure is suppressed, thereby giving rise to an effect for suppressing the vaporization of the components.

The amount of the additives is appropriately determined within a range that the function of the candle is not impaired. But, it is preferably within a range of 0.1 to 5%. Further, though the ratio of the respective additives is not particularly limited, equal amounts of the respective additives were employed in the present embodiment.

Further, in addition to the effect of suppressing the exhalation of the odor at extinguishing, these additives have an effect that, when the odor at extinguishing is vaporized by heat and diffused into air, they trap molecules of various odors hanging in the air, thereby making the air in the whole of a room refreshed.

The Test Example of the invention will be described below. Test Example:

A candle not added and mixed with the above-described additives is referred to as "Sample 1", and a candle added and mixed with the above-described additives according to the invention is referred to as "Sample2", respectively. A candle was stood in a 25 g wide-mouthed bottle, and an odor at extinguishing was collected and analyzed by gas chromatography (GC), thereby obtaining a deodorization effect at extinguishing by the additives from peak areas of each of the resulting samples.

The measurement conditions employed are as follows.

GC column: HP-INNOWax (crosslinked polyethylene glycol) 0.32 mm×30 m

Column temperature: 50 to 250° C.

Injection temperature: 250° C.

Detection temperature: 250° C.

Carrier gas: He

Detector: FID

Figure 1:
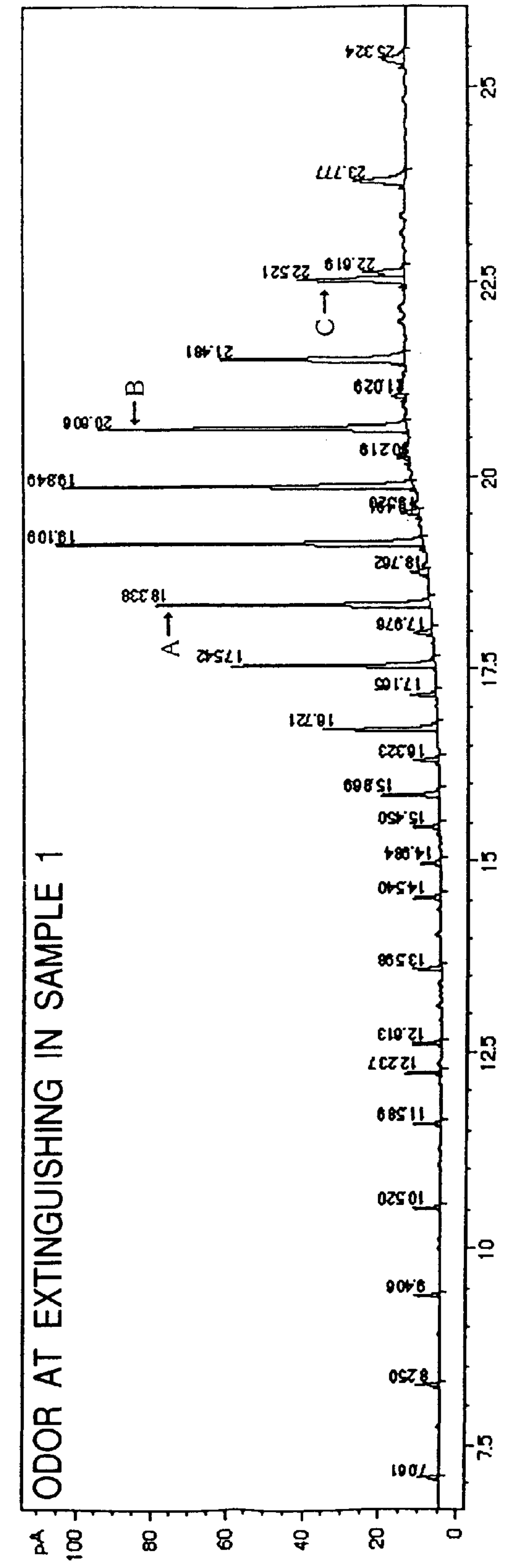
FIG. 1 is a drawing to show a state of the odor at extinguishing of a candle not added and mixed with additives (Sample 1)
Figure 2:
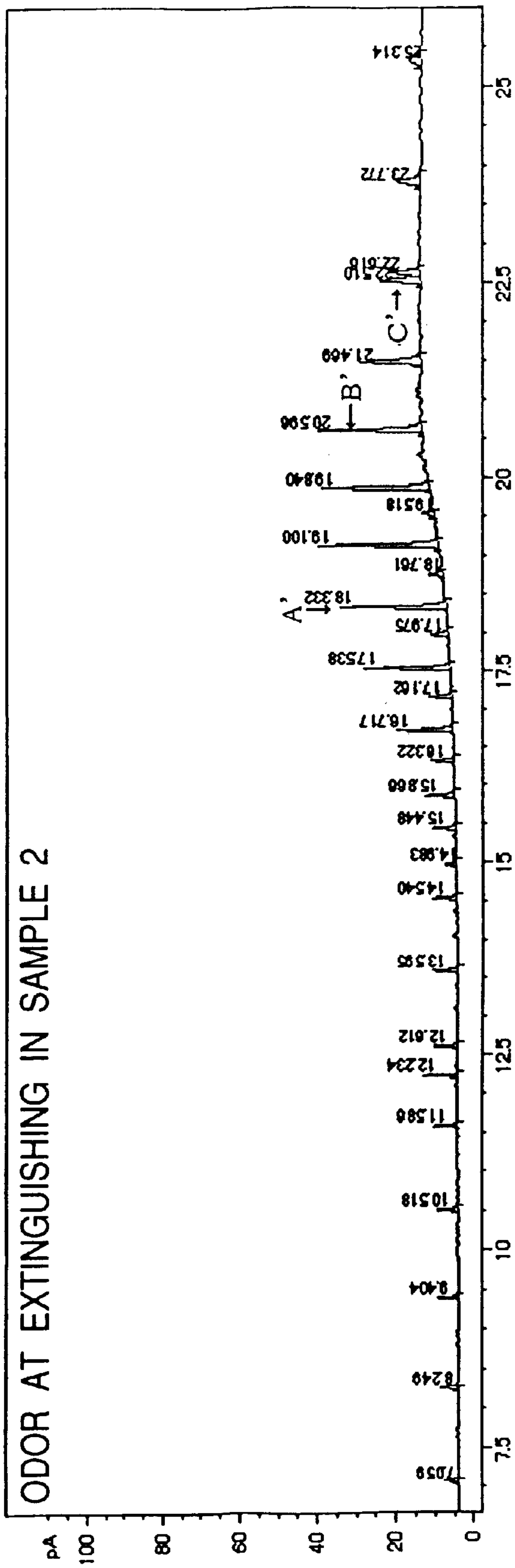
FIG. 2 is a drawing to show a state of the odor at extinguishing of a candle added and mixed with additives.

The results obtained are shown in FIG. 1 and FIG. 2 as well as in Table 1 and Table 2.

The numerical values of the deodorization effect at extinguishing are those obtained by the following equation:

$$X=[(Y-Z)\times 100]/Y$$

In the equation:

X: deodorization effect at extinguishing

Y: each area when Sample 2 was measured

Z: each area when Sample 1 was measured

TABLE 1

| Sample peak | Each area when Sample 1 was measured | Each area when Sample 2 was measured | Deodorization effect at extinguishing (%) |
|---|---|---|---|
| | 8.609 | 5.469 | 36.473 |
| | 10.300 | 7.510 | 27.087 |
| | 11.501 | 9.127 | 20.642 |
| | 11.904 | 9.875 | 17.045 |
| | 12.914 | 10.863 | 15.882 |
| | 14.791 | 13.962 | 5.605 |
| | 13.549 | 11.532 | 14.887 |
| | 14.035 | 12.026 | 14.314 |
| | 13.597 | 11.908 | 12.422 |
| | 11.744 | 7.172 | 38.931 |
| | 13.864 | 12.174 | 12.190 |
| | 33.995 | 17.408 | 48.792 |
| | 13.908 | 12.109 | 12.935 |
| | 65.618 | 33.950 | 48.261 |
| | 14.900 | 12.517 | 15.993 |
| | 120.183 | 50.211 | 58.221 |
| | 15.170 | 11.163 | 26.414 |
| | 168.204 | 63.745 | 62.103 |
| | 13.073 | 8.606 | 34.170 |
| | 232.965 | 74.665 | 67.950 |
| | 7.518 | | — |
| | 222.110 | 65.734 | 70.405 |
| | 8.282 | | — |
| | 226.389 | 74.463 | 67.108 |

TABLE 1-continued

| Sample peak | Each area when Sample 1 was measured | Each area when Sample 2 was measured | Deodorization effect at extinguishing (%) |
|---|---|---|---|
| | 10.725 | | — |
| | 162.981 | 52.365 | 67.870 |
| | 106.076 | 38.826 | 63.398 |
| | 34.576 | 28.358 | 17.984 |
| | 67.471 | 30.831 | 54.305 |
| | 39.647 | 18.403 | 53.583 |
| Total | 1,700.599 | 704.972 | 58.546 |

TABLE 2

| Sample peak | Each area when Sample 1 was measured | Each area when Sample 2 was measured | Deodorization effect at extinguishing (%) |
|---|---|---|---|
| A and A' | 168.204 | 63.745 | 62.103 |
| B and B' | 226.389 | 74.463 | 67.108 |
| C and C' | 106.076 | 38.826 | 63.398 |

It is evident from the above results that the invention has an effect for suppressing the exhalation of a nasty odor (an odor at extinguishing) generated when a flame of a candle has been extinguished.

In the light of the above, the candle according to the invention can suppress the exhalation of a nasty odor (an odor at extinguishing) generated when a flame has been extinguished. Further, when the odor at extinguishing is vaporized by heat and diffused into air, the additives to be added and mixed in the candle according to the invention can trap molecules of various odors hanging in the air, thereby making the air in the whole of a room refreshed.

While the invention has been described in detail and with reference to specific embodiments thereof, it will be apparent to one skilled in the art that various changes and modifications can be made therein without departing from the spirit and scope thereof.

What is claimed is:

1. A candle comprising a candle-forming component including a paraffin wax and stearic acid, added and mixed with tetrahydro methylabietate and dihydro methylabietate, isopropyl myristate, α-amylcinnamic alcohol iso bornyl cyclohexanol, and tri ethyl citrate.

* * * * *